US008858423B2

(12) United States Patent
Yasunaga et al.

(10) Patent No.: US 8,858,423 B2
(45) Date of Patent: Oct. 14, 2014

(54) ENDOSCOPE HOLDING APPARATUS

(75) Inventors: Koji Yasunaga, Hino (JP); Motokazu Nakamura, Hachioji (JP); Kenji Hirose, Hachioji (JP); Hisao Isobe, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 64 days.

(21) Appl. No.: 13/271,694

(22) Filed: Oct. 12, 2011

(65) Prior Publication Data

US 2012/0088963 A1 Apr. 12, 2012

Related U.S. Application Data

(63) Continuation of application No. PCT/JP2011/062823, filed on Jun. 3, 2011.

(30) Foreign Application Priority Data

Jun. 10, 2010 (JP) ................................. 2010-133169

(51) Int. Cl.
*A61B 1/00* (2006.01)
*A61B 1/313* (2006.01)
*A61B 19/00* (2006.01)

(52) U.S. Cl.
CPC ........ *A61B 1/00149* (2013.01); *A61B 2019/265* (2013.01); *A61B 19/2203* (2013.01); *A61B 1/3132* (2013.01)
USPC ....................................................... 600/102

(58) Field of Classification Search
CPC ..... A61B 1/00147; A61B 19/22; A61B 19/26
USPC ....................................................... 600/102
See application file for complete search history.

(56) References Cited

U.S. PATENT DOCUMENTS

| 4,867,405 | A | * | 9/1989 | Nakamura | ............... 248/281.11 |
| 4,881,709 | A | | 11/1989 | Nakamura | |
| 5,213,293 | A | * | 5/1993 | Muentener et al. | ...... 248/123.11 |
| 2004/0246469 | A1 | | 12/2004 | Hirose | |
| 2005/0228365 | A1 | | 10/2005 | Wang et al. | |

FOREIGN PATENT DOCUMENTS

| JP | S56-44704 | | 4/1981 |
| JP | 07-289563 | A | 11/1995 |
| JP | 07-303599 | A | 11/1995 |
| JP | 2003-052718 | A | 2/2003 |
| JP | 2004-167287 | A | 6/2004 |
| JP | 2004-181257 | A | 7/2004 |
| JP | 2004-230176 | A | 8/2004 |
| JP | 2004-243136 | A | 9/2004 |
| JP | 2007-125404 | A | 5/2007 |

OTHER PUBLICATIONS

European Search Report dated Apr. 4, 2012 from corresponding European Patent Application No. EP 11 79 2368.0.

* cited by examiner

*Primary Examiner* — Matthew J Kasztejna
(74) *Attorney, Agent, or Firm* — Scully, Scott, Murphy & Presser, P.C.

(57) ABSTRACT

A distal arm that holds a rigid endoscope includes a multi-joint articulated arm including first to fourth distal arm portions sequentially connected from a base portion side, and these first to fourth distal arm portions are configured so as to move on a vertical plane with horizontal rotational shafts as supports. In addition, behaviors of the respective distal arm portions are linked by a linking mechanism so that the first distal arm portion and the third distal arm portion behave in parallel to each other, and the second distal arm portion and the fourth distal arm portion behave in parallel to each other.

9 Claims, 14 Drawing Sheets

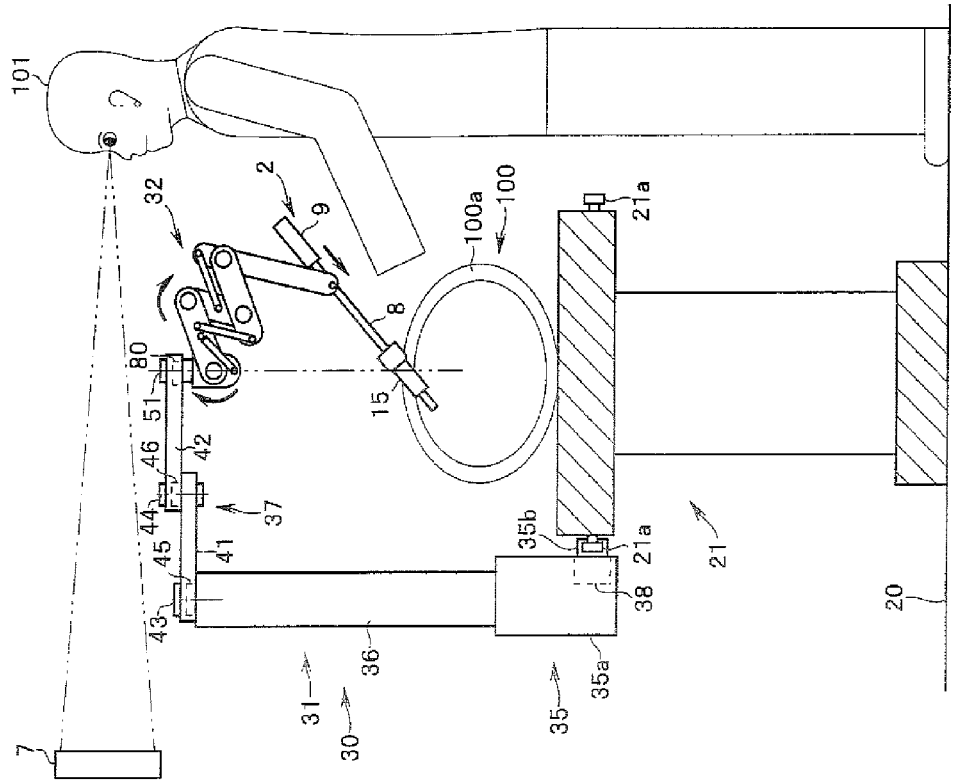
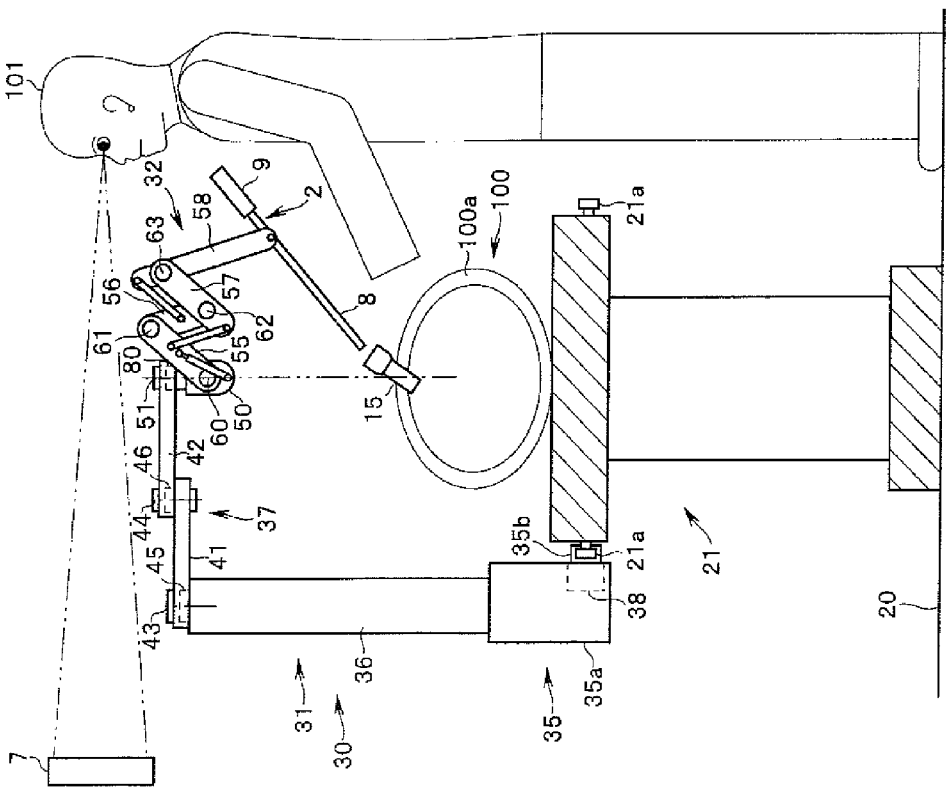

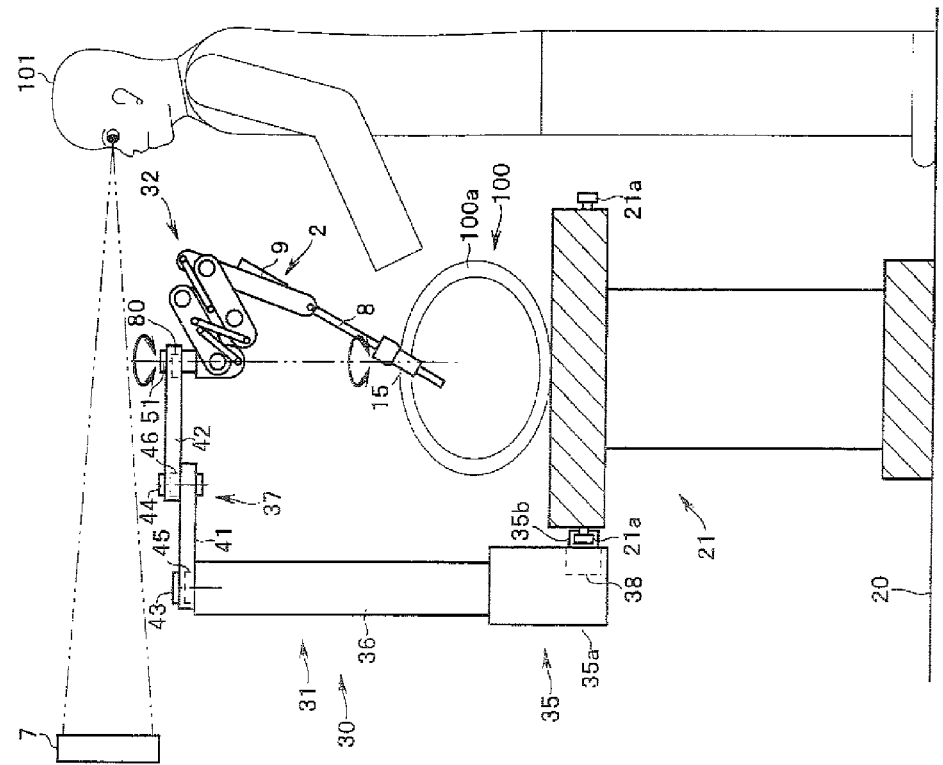
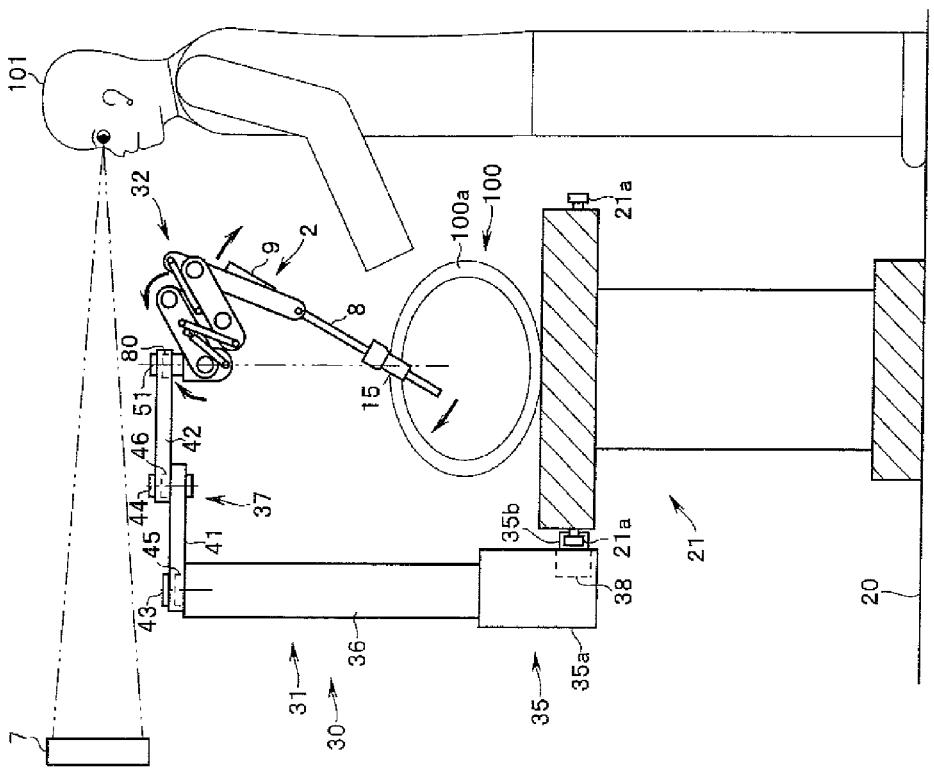

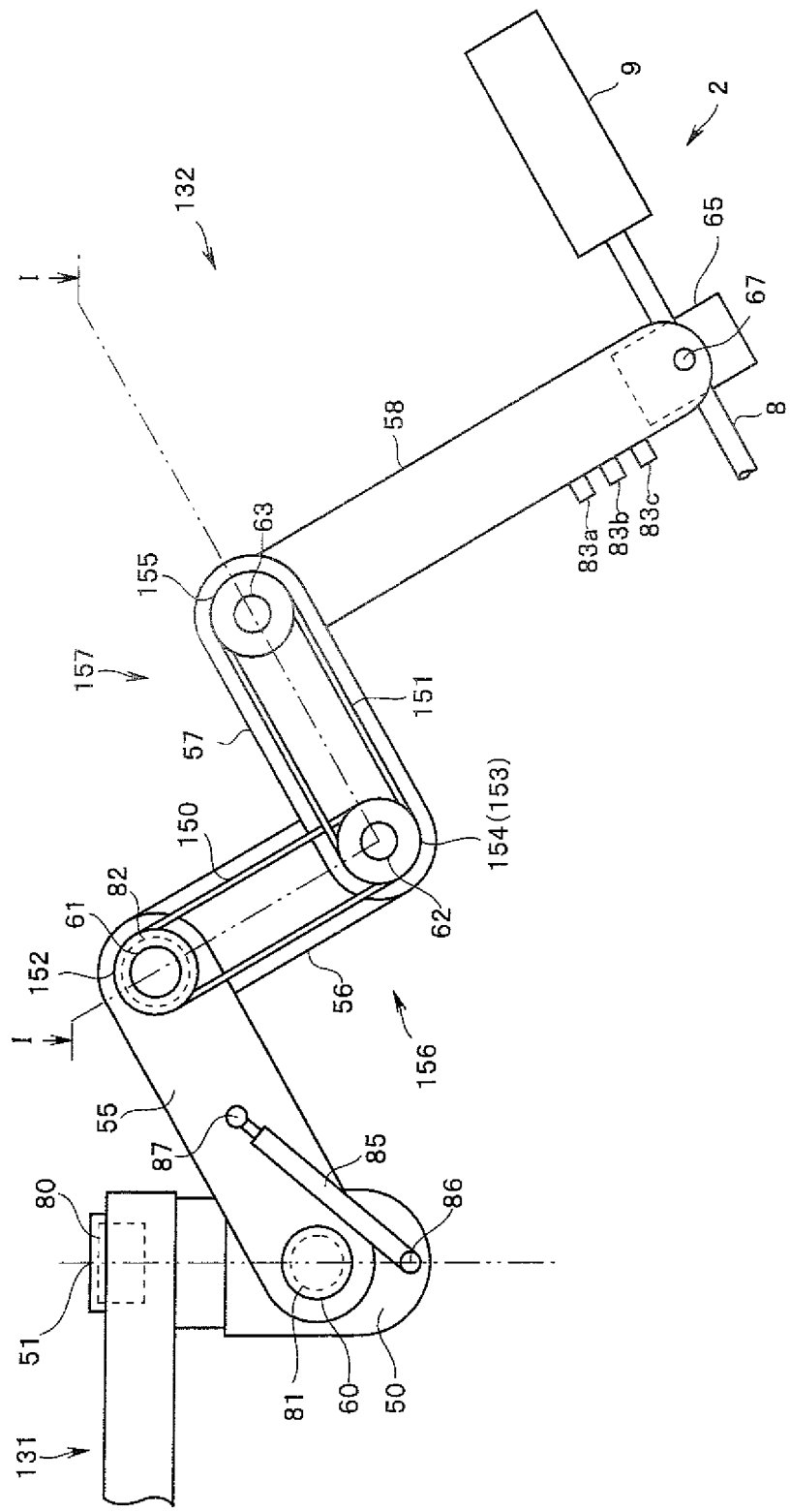

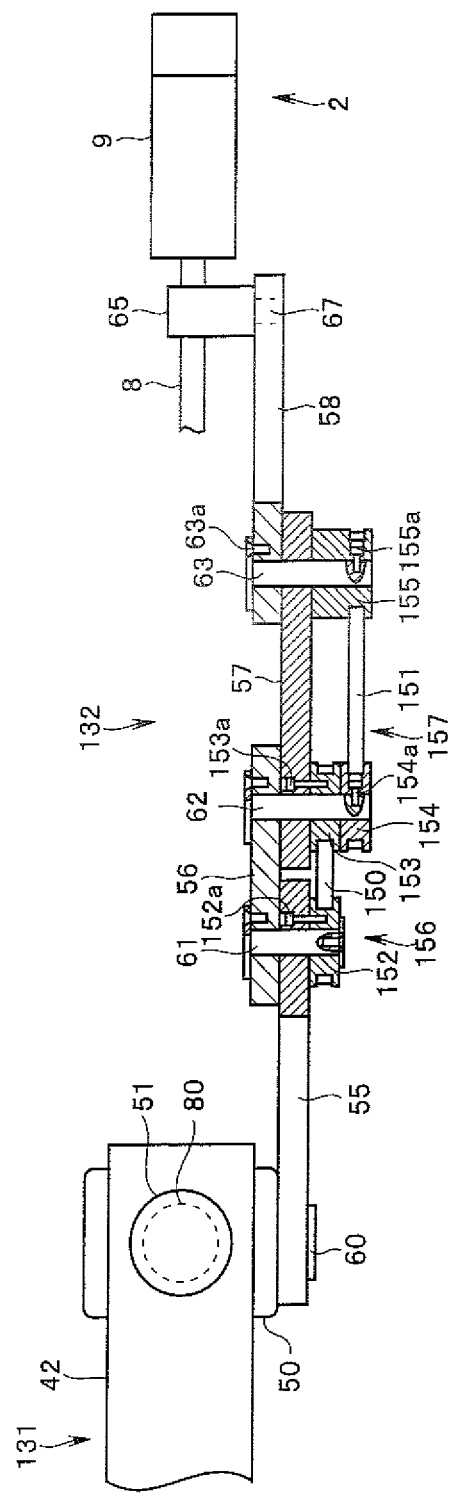

the rigid endoscope used by an assistant.
ENDOSCOPE HOLDING APPARATUS

CROSS REFERENCE TO RELATED APPLICATION

This application is a continuation application of PCT/JP2011/062823 filed on Jun. 3, 2011 and claims benefit of Japanese Application No. 2010-133169 filed in Japan on Jun. 10, 2010, the entire contents of which are incorporated herein by this reference.

BACKGROUND OF THE INVENTION

1. Field of the Invention

The present invention relates to an endoscope holding apparatus that holds an endoscope used in a surgery instead of a surgeon.

2. Description of the Related Art

Conventionally, rigid endoscopes for observing the inside of a body cavity have widely been used in endoscopic surgical operations. An endoscope of this type is inserted into an abdominal cavity via a guide member, such as a trocar, pierced through the abdominal wall. In surgeries, in general, an endoscope is held by a helper (assistant) called a "scopist". A scopist performs operations to, e.g., advance/retract, turn or tilt an endoscope, enabling observation of a desired site inside a body cavity.

Furthermore, in recent years, in order to reduce the burden of scopists, endoscope holding apparatuses that mechanically hold an endoscope have been proposed. For example, Japanese Patent Application Laid-Open Publication No. 2007-125404 discloses an endoscope holding apparatus including a lifting/lowering section and a multi-joint articulated arm that moves on a horizontal plane. This endoscope holding apparatus provides the aforementioned respective motions, such as advancing/retracting, turning and tilting, necessary for an endoscope during an observation by combination of lifting/lowering motion made by the lifting/lowering section and horizontal motions made by the articulated arm.

Furthermore, for example, as illustrated in FIGS. 13 and 14, a distal arm 202 that holds an endoscope 220 can be configured so as to move on a vertical plane. Here, in an endoscope holding apparatus 200, which is illustrated in the figures, a first arm portion 203 and a second arm portion 204 are rotatably connected via a horizontal rotational shaft 206, whereby an articulated distal arm 202 is formed. Furthermore, a base portion 210 is rotatably connected to a proximal end side of the distal arm 202 via a horizontal rotational shaft 205, and the base portion 210 is rotatably connected to a stand 201 including a distal end portion that can be secured at a position above a patient, via a vertical rotational shaft 211. Meanwhile, at a distal end portion of the distal arm 202, an endoscope holding portion 207 that holds an endoscope 220 is rotatably and pivotally supported via a horizontal rotational shaft 208.

The endoscope holding apparatus 200 configured as described above provides advancing/retracting motions, turning motions and tilting motions of the endoscope 220 with a smallest number of joints (shafts). In addition, such endoscope holding apparatus 200 provides no unnecessary joint motions, preventing, e.g., the respective arm portions 203 and 204 from interfering with each other and being locked, and makes the arm portions 203 and 204 follow motions of the endoscope 220 by means of stable behaviors of the arm portions 203 and 204 based on swinging (rotation).

SUMMARY OF THE INVENTION

An endoscope holding apparatus according an aspect of the present invention includes: a stand that supports a base portion; a distal arm with a proximal end side thereof supported by the base portion, the distal arm including a multi-joint arm including first to fourth distal arm portions sequentially connected from the base portion side, the distal arm moving an endoscope held on a distal end side thereof on a vertical plane; and an interlocking section that links behaviors of the respective distal arm portions so that the first distal arm portion and the third distal arm portion behave in parallel to each other, and the second distal arm portion and the fourth distal arm portion behave in parallel to each other.

Also, an endoscope holding apparatus according to another aspect of the present invention includes: a stand that supports a base portion; a distal arm with a proximal end side thereof supported by the base portion, the distal arm including a multi-joint arm including first to fourth distal arm portions sequentially connected from the base portion side, the distal arm moving an endoscope held on a distal end side thereof on a vertical plane; and interlocking means for linking behaviors of the respective distal arm portions so that the first distal arm portion and the third distal arm portion behave in parallel to each other, and the second distal arm portion and the fourth distal arm portion behave in parallel to each other.

BRIEF DESCRIPTION OF THE DRAWINGS

FIG. 3 relates to the first embodiment of the present invention and is an illustrative diagram of a state before insertion of an endoscope;

FIG. 4 relates to the first embodiment of the present invention and is an illustrative diagram of motion of an articulated arm during insertion of an endoscope;

FIG. 5 relates to the first embodiment of the present invention and is an illustrative diagram of motion of an articulated arm during an operation to tilt an endoscope;

FIG. 6 relates to the first embodiment of the present invention and is an illustrative diagram of motion of an articulated arm during an operation to turn an endoscope;

FIG. 11A relates to a second embodiment of the present invention and is a side view showing a schematic configuration of an articulated arm;

FIG. 11B relates to the second embodiment of the present invention and is a cross-sectional diagram of a main part taken along line I-I in FIG. 11A;

DETAILED DESCRIPTION OF THE PREFERRED EMBODIMENTS

Figure 1:
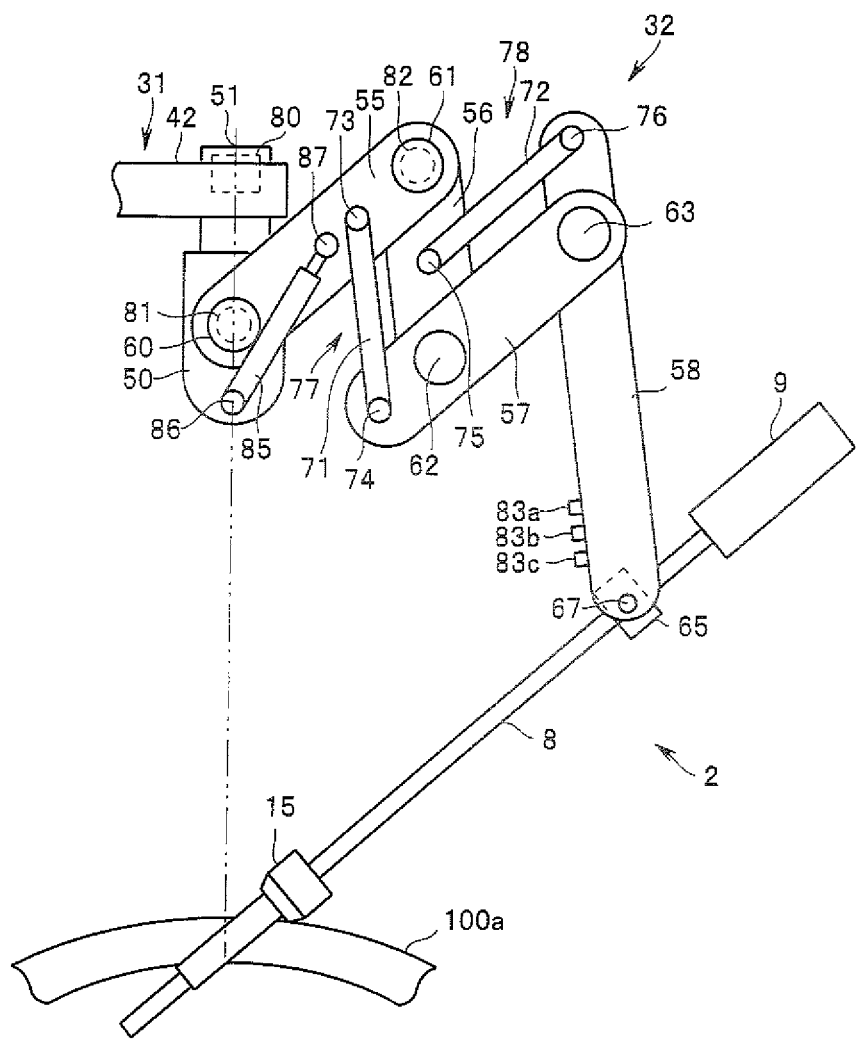
FIG. 1 relates to a first embodiment of the present invention and is a side view showing a schematic configuration of an articulated arm that holds an endoscope.
Figure 2:
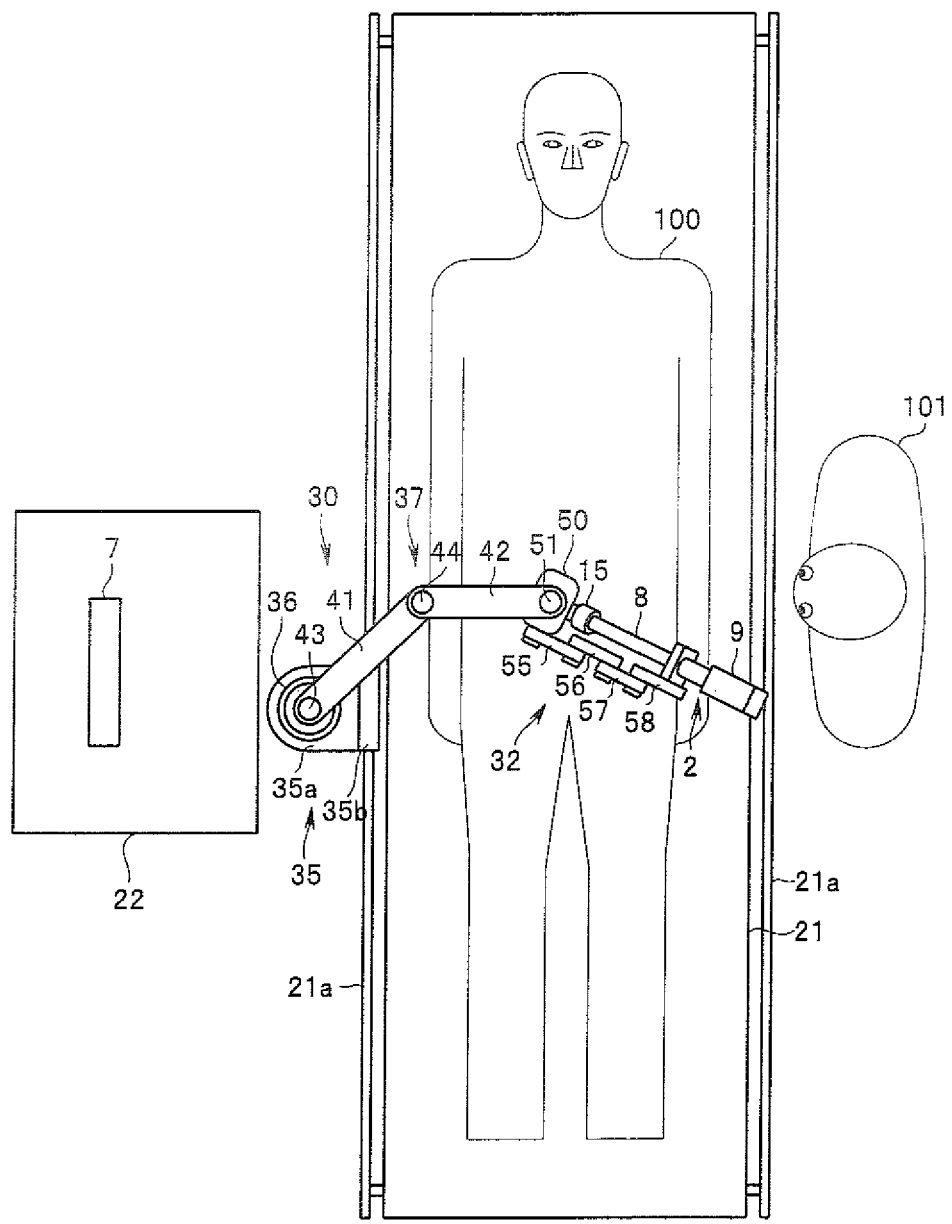
FIG. 2 relates to the first embodiment of the present invention and is a plan view showing a relationship between an endoscope holding apparatus and a surgeon during a surgery.
Figure 7A:
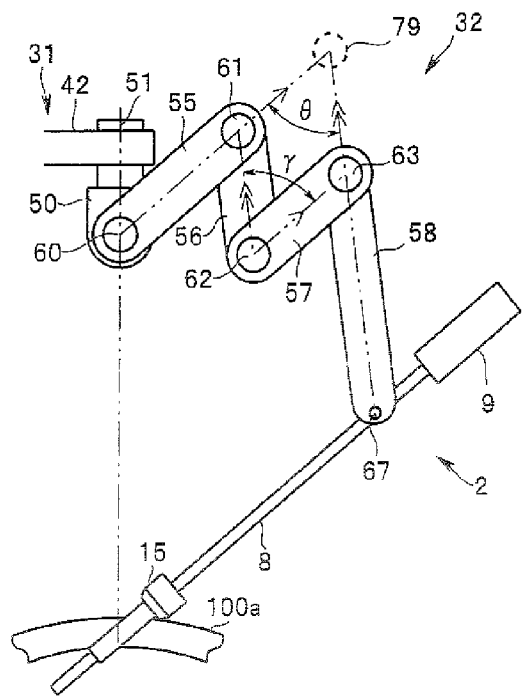
FIG. 7A relates to the first embodiment of the present invention and is an illustrative diagram of motion of respective arm portions during a titling operation.
Figure 7B:
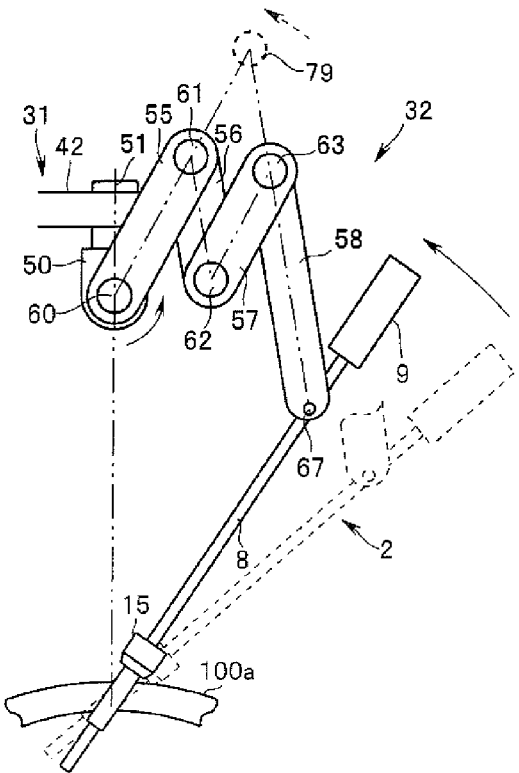
FIG. 7B relates to the first embodiment of the present invention and is an illustrative diagram of motion of respective arm portions during a titling operation.
Figure 7C:
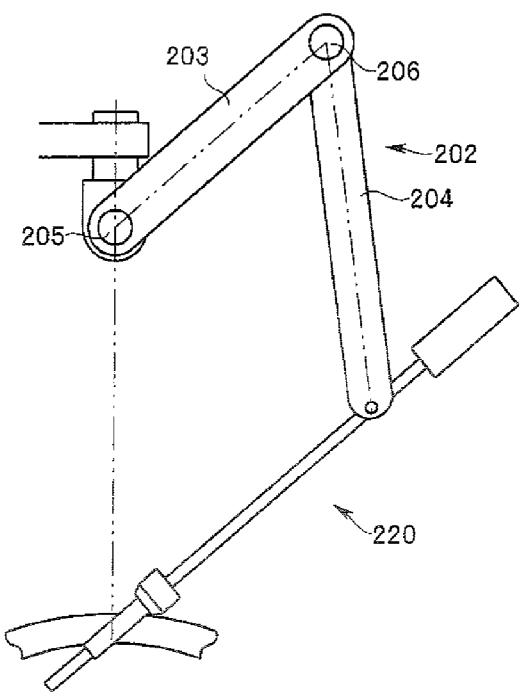
FIG. 7C relates to the first embodiment of the present invention and is an illustrative diagram showing a comparative example for FIG. 7A.
Figure 7D:
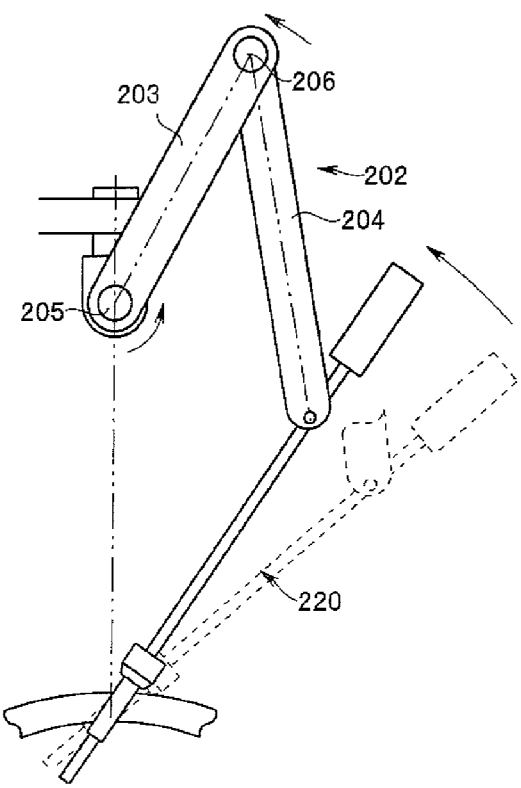
FIG. 7D relates to the first embodiment of the present invention and is an illustrative diagram showing a comparative example for FIG. 7B.
Figure 8:
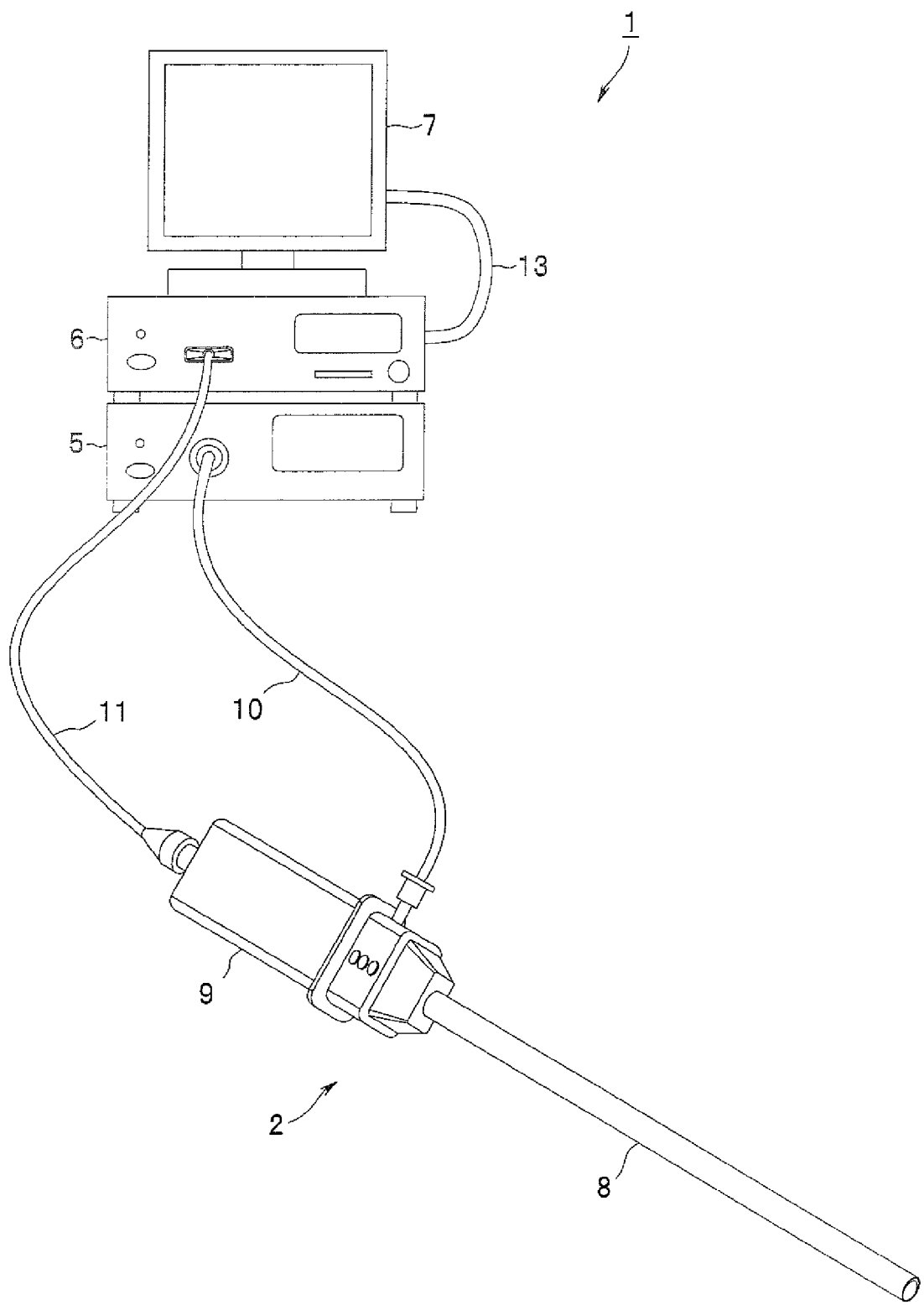
FIG. 8 relates to the first embodiment of the present invention and is an illustrative diagram showing an endoscope system.
Figure 9:
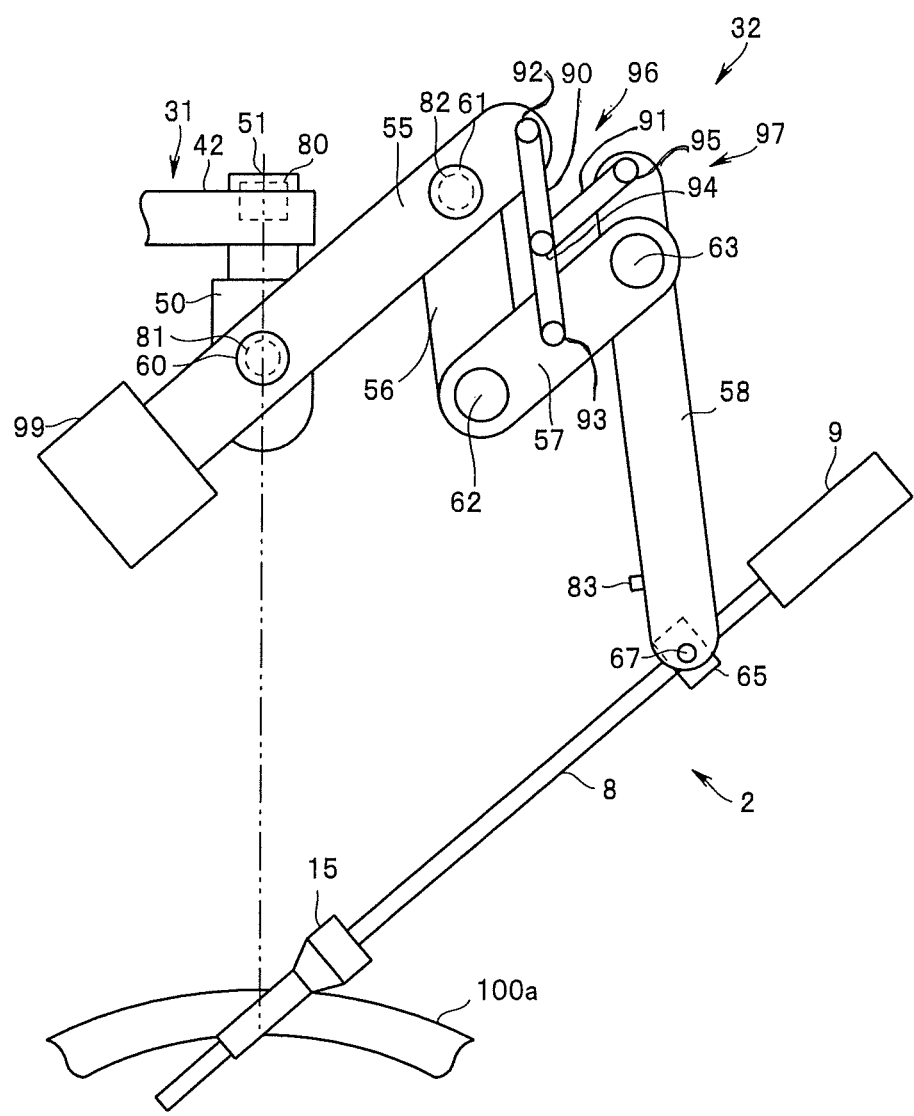
FIG. 9 relates to the first embodiment of the present invention and is an illustrative diagram showing a modified example of links.

Hereinafter, embodiments of the present invention will be described with reference to the drawings. FIGS. 1 to 9 relate to a first embodiment of the present invention: FIG. 1 is a side view showing a schematic configuration of an articulated arm that holds an endoscope; FIG. 2 is a plan view showing a relationship between an endoscope holding apparatus and a surgeon during a surgery; FIG. 3 is an illustrative diagram of a state before insertion of an endoscope; FIG. 4 is an illustrative diagram of motion of an articulated arm during insertion of an endoscope; FIG. 5 is an illustrative diagram of motion of an articulated arm during an operation to tilt an endoscope; FIG. 6 is an illustrative diagram of motion of an articulated arm during an operation to turn an endoscope; FIGS. 7A and 7B are illustrative diagrams of motion of respective arm portions during a titling operation; FIGS. 7C and 7D are illustrative diagrams showing a comparative example for FIGS. 7A and 7B; FIG. 8 is an illustrative diagram showing an endoscope system; and FIG. 9 is an illustrative diagram showing a modified example of links.

First, an endoscope system for a laparoscopic surgical operation will be described as an example of an endoscope system including an endoscope, to which the present invention is applicable. As illustrated in FIG. 8, an endoscope system 1 includes a rigid endoscope 2 as an endoscope, a light source apparatus 5 that supplies illuminating light to an illumination optical system in the rigid endoscope 2, a camera control unit (hereinafter abbreviated as "CCU") 6, which is a signal processing apparatus including a built-in image processing circuit, and a display apparatus (monitor) 7 connected to the CCU 6 via a communication cable 13, the display apparatus (monitor) 7 displaying a picked-up image.

The rigid endoscope 2 includes a rigid insertion portion 8, and an operation section 9 provided so as to be continuous with a proximal end portion of the insertion portion 8. An image guide and a light guide bundle are inserted through the inside of the insertion portion 8. At a distal end portion of the insertion portion 8, a shooting optical system that collects light via an image guide to form an image of a subject on a camera head, which will be described later, and an illumination optical system that applies illuminating light from the light guide bundle toward the subject are disposed.

The operation section 9 includes the non-illustrated built-in camera head including a solid image pickup device such as a CCD or a CMOS. Furthermore, a light source cable 10 extending from the light source apparatus 5 is detachably connected to the operation section 9. Illuminating light supplied from the light source apparatus 5 to the operation section 9 via the light source cable 10 is conveyed to the illumination optical system via the light guide bundle in the insertion portion 8 and illuminates a site to be observed. Then, an optical image of the site to be observed is conveyed to the camera head in the operation section 9 through the shooting optical system and the image guide. Consequently, the camera head picks up the optical image of the site to be observed, and image pickup signals of the picked-up optical image are transmitted to the CCU 6 via an image pickup cable 11.

The CCU 6 generates video signals based on the transmitted image signals and outputs the video signals to the display apparatus 7. The display apparatus 7 includes, for example, a liquid-crystal display, and upon receipt of the video signals outputted from the CCU 6, displays an observed image provided by a rigid endoscope 2.

In a laparoscopic surgical operation using such endoscope system 1, for example, as illustrated in FIGS. 2 to 6, a bed 21 on which a patient 100 lies is arranged on a floor 20 of an operating room, and a trolley 22 is arranged across the bed 21 from a surgeon 101. Then, for example, the light source apparatus 5 and the CCU 6 (not illustrated) are housed in a trolley 22, and the display apparatus 7 is mounted on a top portion of the trolley 22 so as to face the surgeon 101.

Furthermore, bed rails 21a are provided at side portions of the bed 21, and the endoscope holding apparatus 30 is attached to one of these bed rails 21a. Then, the rigid endoscope 2 is held at an arbitrary posture relative to the patient 100 by means of the endoscope holding apparatus 30.

As illustrated in FIGS. 2 to 6, the endoscope holding apparatus 30 includes a stand 31 that can be secured at an arbitrary position on the bed rail 21a, and a distal arm 32 supported by the stand 31.

The stand 31 includes a bed attachment portion 35 that can be detachably attached to the bed rail 21a, a strut 36 provided so as to vertically stand from the bed attachment portion 35, and a base arm 37 horizontally extending from the strut 36.

The bed attachment portion 35 includes a bed attachment portion body 35a and a fitting portion 35b provided on a side of the bed attachment portion body 35a, and the fitting portion 35b is loosely fitted on the bed rail 21a, and thereby detachably attached to the bed rail 21a. Furthermore, in the bed attachment portion body 35a, a locking mechanism 38 including, for example, an electromagnetic clutch is provided, and movement of the fitting portion 35b is prohibited by means of the locking mechanism 38, enabling the bed attachment portion 35 to be held at an arbitrary position on the bed rail 21a.

The locking mechanism 38 is in a locked state when, for example, a non-illustrated switch is not operated, and held the bed attachment portion 35 on the arbitrary position on the bed rail 21a. Meanwhile, the locking mechanism 38 is in a state in which the lock is released (a free state) while the switch is being operated, allowing movement of the bed attachment portion 35 on the bed rail 21a.

The base arm 37 includes an articulated arm including first and second base arm portions 41 and 42 sequentially connected from the strut 36 side. For more specific description, a proximal end side of the first base arm portion 41 is rotatably and pivotally supported on a top portion of the strut 36 via a vertical rotational shaft 43. Also, a proximal end side of the second base arm portion 42 is rotatably and pivotally supported on a distal end side of the first base arm portion 41 via a vertical rotational shaft 44. The base arm portions 41 and 42 can each displace on a horizontal plane by means of rotary (swing) motion with the respective vertical rotational shafts 43 and 44 as supports. Then, a displacement of the base arm portions 41 and 42 makes a distal end portion of the base arm 37 horizontally move to an arbitrary position above the patient.

Furthermore, the respective vertical rotational shafts 43 and 44 are provided with locking mechanisms 45 and 46 each including, for example, an electromagnetic brake, respectively, and rotational positions of the base arm portions 41 and 42 can be held (locked) by the respective locking mechanisms 45 and 46.

The locking mechanism 45 and 46 are in a locked state when, for example, a non-illustrated switch is not operated, prohibiting rotation of the base arm portions 41 and 42 with the vertical rotational shafts 43 and 44 as supports and holding the base arm portions 41 and 42 at respective arbitrary positions. Meanwhile, the locking mechanisms 45 and 46 are in a state in which the lock is released (a free state) while the switch is being operated, allowing rotary motion of the base arm portions 41 and 42 with the respective vertical rotational shafts 43 and 44 as supports.

As illustrated in FIG. 1, a base portion 50 supporting the distal arm 32 is rotatably and pivotally supported at the distal end portion of the base arm 37 via a vertical rotational shaft 51.

The distal arm 32 includes a multi-joint articulated arm including first to fourth distal arm portions 55 to 58 sequentially connected from the base portion 50 side. For more specific description, a proximal end side of the first distal arm portion 55 is rotatably and pivotally supported at the base portion 50 via a horizontal rotational shaft 60. Also, a proximal end side of the second distal arm portion 56 is rotatably and pivotally supported on a distal end side of the first distal arm portion 55 via a horizontal rotational shaft 61. A proximal end side of the third distal arm portion 57 is rotatably and pivotally supported on a distal end side of the second distal arm portion 56 via a horizontal rotational shaft 62. Furthermore, a proximal end side of the fourth distal arm portion 58 is rotatably and pivotally supported on a distal end side of the third distal arm portion 57 via a horizontal rotational shaft 63. Furthermore, an endoscope holding portion 65 that holds the rigid endoscope 2 is rotatably and pivotally supported at a distal end portion of the fourth distal arm portion 58 via a horizontal rotational shaft 67.

The distal arm 32 can horizontally displace the respective distal arm portions 55 to 58 in their entireties by means of rotary (swing) motion of the base portion 50 with the vertical rotational shaft 51 as a support. Furthermore, the distal arm 32 can displace the respective distal arm portions 55 to 58 on a vertical plane by means of rotary (swing) motion with the respective horizontal rotational shafts 60 to 63 as supports. Then, the horizontal and vertical displacements of the respective distal arm portions 55 to 58 enables the distal arm 32 to three-dimensionally move the endoscope holding portion 65 relative to the stand 31.

Here, the distal arm 32 is provided with first and second auxiliary arm portions 71 and 72 in order to link the respective behaviors of the respective distal arm portions 55 to 58.

The first auxiliary arm portion 71 is arranged in parallel to the second distal arm portion 56, and one end portion of the first auxiliary arm portion 71 is rotatably and pivotally supported at a position part way through the first distal arm portion 55 via a horizontal rotational shaft 73, and the other end side of the first auxiliary arm portion 71 is rotatably and pivotally supported by a proximal end portion of the third distal arm portion 57 via a horizontal rotational shaft 74. Consequently, the first auxiliary arm portion 71 provides a first parallelogram link 77 jointly with the first to third distal arm portions 55 to 57.

The second auxiliary arm portion 72 is arranged in parallel to the third distal arm portion 57, one end portion of the second auxiliary arm portion 72 is rotatably and pivotally supported at a position part way through the second distal arm portion 56 via a horizontal rotational shaft 75, and the other end side of the second auxiliary arm portion 72 is rotatably and pivotally supported by a proximal end portion of the fourth distal arm portion 58 via a horizontal rotational shaft 76. Consequently, the second auxiliary arm portion 72 provides a second parallelogram link 78 jointly with the second to fourth distal arm portion 56 to 58.

The first and second parallelogram links 77 and 78 provide a linking mechanism as interlocking means. Then, the linking mechanism links the behaviors of the respective distal arm portion 55 to 58 so that the first distal arm portion 55 and the third distal arm portion 57 behave in parallel to each other, and the second distal arm portion 56 and the fourth distal arm portion 58 behave in parallel to each other. Consequently, as illustrated in, for example, FIG. 7A, the distal arm 32 moves with an angle θ formed by the first and fourth distal arm portions 55 and 58 and an angle γ formed by the second and third distal arm portions 56 and 57 consistently maintained to be equal to each other. In other words, an operation of the linking mechanism enables the first and fourth distal arm portions 55 and 58 to make rotary (swing) motion with an intersection between extensions thereof as a virtual rotational shaft 79.

Furthermore, the vertical rotational shaft 51 via which the base portion 50 is pivotally supported by the stand 31 is provided with a locking mechanism 80 including, for example, an electromagnetic brake. When, for example, a switch 83a provided at the fourth distal arm portion 58 is not operated, the locking mechanism 80 is in a locked state and prohibits rotation of the base portion 50 with the vertical rotational shaft 51 as a support, and holds a horizontal rotational position of the base portion 50 relative to the stand 31. Meanwhile, while the switch 83a is being operated, the locking mechanism 80 is in a state in which the lock is released (in a free state) and allows rotary motion of the base portion 50 with the vertical rotational shaft 51 as a support.

Furthermore, the horizontal rotational shaft 60 via which the first distal arm portion 55 is pivotally supported by the base portion 50 and the horizontal rotational shaft 61 via which the second distal arm portion 56 is pivotally supported by the first distal arm portion 55 are provided with locking mechanisms 81 and 82 each including, for example, an electromagnetic brake, and the locking mechanisms 81 and 82 enable rotational positions of the respective distal arm portions 55 to 58 to be held (locked). Here, the respective distal arm portions 55 to 58 are connected via the respective auxiliary arms 71 and 72, and thus, the distal arm 32 in the present embodiment enables the single locking mechanism 82 provided at the horizontal rotational shaft 61 to also lock rotary motions with the other two horizontal rotational shafts 62 and 63 as supports. The locking mechanism 82 may be provided at any one of the horizontal rotational shafts 62 and 63 instead of the horizontal rotational shaft 61.

When, for example, switches 83b and 83c provided at the fourth distal arm portion 58 are not operated, the locking mechanisms 81 and 82 are in a locked state, and prohibit rotation of the distal arm portions 55 to 58 with the horizontal rotational shafts 60 to 63 as supports to hold the distal arm portions 55 to 58 at respective arbitrary positions. Meanwhile, while the switches 83b and 83c are being operated, the locking mechanisms 81 and 82 are in a state in which the locks are released (free state), and allow rotary motions of the distal arm portions 55 to 58 with the horizontal rotational shafts 60 to 63 as supports.

Furthermore, a gas spring 85 is provided as balancing means so as to bridge between the base portion 50 and the first distal arm portion 55 via horizontal rotational shafts 86 and 87. The gas spring 85 elastically connects the base portion 50 and the distal arm portion 55, and thereby balances out a moment around the horizontal rotational shaft 60, which is generated by the weight of the distal arm 32.

Next, an operation of the endoscope holding apparatus 30 configured as described above will be described.

As illustrated in FIG. 3, prior to insertion of the rigid endoscope 2, first, the bed attachment portion 35 is secured at a proper position relative to the trocar position. Next, a surgeon, a scopist or the like (hereinafter, the surgeon or the like) unlocks the respective portions by operating non-illustrated switches for the locking mechanisms 43 and 44 on the stand 31 side. Then, the surgeon or the like moves the respective base arm portions 41 and 42 on a horizontal plane with the vertical rotational shafts 43 and 44 as supports to perform positioning so that the vertical rotational shaft 51 of the base portion 50 is positioned immediately above the trocar 15 pierced through an abdominal wall 100*a* of the patient 100. After the positioning operation, the surgeon or the like stops the operation of the switches for the respective locking mechanisms 42 and 44, and the position of the stand 31 resulting from the positioning is thereby maintained.

Next, the surgeon or the like unlock the respective portions by operating the switches 83*a* to 83*c* for the respective locking mechanisms 80 to 82 on the distal arm 32 side. In this state, the surgeon or the like grasps, for example, the operation section 9 of the rigid endoscope 2 to move a distal end of the insertion portion 8 to the position of the trocar 15, and then, inserts the insertion portion 8 into an abdominal cavity of the patient 100 by means of advancing/retracting motion of the rigid endoscope 2 relative to the trocar 15. Here, the respective distal arm portions 55 to 58 of the distal arm 32 are each displaced following the movement of the rigid endoscope 2.

In other words, during, for example, an insertion motion (advancing/retracting motion) of the rigid endoscope 2 relative to the trocar 15, for example, as illustrated in FIG. 4, the first distal arm portion 55 makes a rotary (swing) motion to move the distal end side thereof downward with the horizontal rotational shaft 60 as a support, following the insertion motion. Also, the second distal arm portion 56 makes a rotary (swing) motion to move the distal end side thereof toward the side opposite to the surgeon 101 side with the horizontal rotational shaft 61 as a support. Here, the third distal arm portion 57 moves in parallel to the first distal arm portion 55 by means of an operation of the first parallelogram link 77, and the fourth distal arm portion 58 moves in parallel to the second distal arm portion 56 by means of an operation of the second parallelogram link 78. Consequently, the distal arm 32 substantially exhibits a behavior that is substantially equal to a motion resulting from combination of the rotary (swing) motion of the first distal arm portion 55 with the horizontal rotational shaft 60 as a support and the rotary (swing) motion of the fourth distal arm portion 58 with the virtual rotational shaft 79 as a support.

Furthermore, when the surgeon or the like makes the rigid endoscope 2 make a tilting motion toward the surgeon 101 side with the trocar 15 as a support, for example, as illustrated in FIG. 5, the first distal arm portion 55 makes a rotary (swing) motion to move the distal end side thereof downward with the horizontal rotational shaft 60 as a support, following the tilting motion of the rigid endoscope 2. Furthermore, the second distal arm portion 56 makes a rotary (swing) motion so that the distal end side thereof moves toward the surgeon 101 side with the horizontal rotational shaft 61 as a support. Here, the third distal arm portion 57 moves in parallel to the first distal arm portion 55 by means of an operation of the first parallelogram link 77, and the fourth distal arm portion 58 moves in parallel to the second distal arm portion 56 by means of an operation of the second parallelogram link 78. Consequently, the distal arm 32 exhibits a behavior that is substantially equal to a motion resulting from combination of the rotary (swing) motion of the first distal arm portion 55 with the horizontal rotational shaft 60 as a support and the rotary (swing) motion of the fourth distal arm portion 58 with the virtual rotational shaft 79 as a support.

The behavior of the distal arm 32 resulting from, for example, the insertion motion, the tilting motion and the like of the rigid endoscope 2 additionally includes factors of a parallel movement of the first and third distal arm portions 55 and 57 relative to each other and a parallel movement of the second and fourth distal arm portions 56 and 58 relative to each other by means of operations of the horizontal rotational shafts 61 and 63; however, in fact, such movements enhance the degree of freedom in behavior of the distal arm 32, and in addition, the respective distal arm portions 55 to 58 do not interfere with one another by means of operations of the respective parallelogram links 77 and 78, and thus, no specific problems arise.

Furthermore, when the surgeon or the like makes the rigid endoscope 2 make a turning motion with the trocar 15 as a support, for example, as illustrated in FIG. 6, the distal arm 32 (the respective distal arm portions 55 to 58) integrally makes a rotary (swing) motion so as to turn with the vertical rotational shaft 51 as a support, following the turning motion of the rigid endoscope 2. In this case, the vertical rotational shaft 51 of the base portion 50 is positioned immediately above the trocar 15 by means of positioning of the stand 31, enabling a motion of the distal arm 37 resulting from the turning motion of the rigid endoscope 2 to substantially be provided basically by means of a rotary motion with the vertical rotational shaft 51 as a support alone. In such case, even if the locking mechanisms 81 and 82 are in a locked state, displacements resulting from the turning motion of the rigid endoscope 2 are absorbed as appropriate by means of, e.g., a rotary motion with the horizontal rotational shaft 67, which consistently supports the endoscope holding portion 65 in a free state, as a support, and thus, no stress is imposed on, e.g., the abdominal wall 100*a* of the patient 100.

Here, for an example more specifically indicating the behavior of the distal arm 32 associated with motion of the rigid endoscope 2, FIGS. 7A and 7B illustrate a behavior of the distal arm 32 before and after, e.g., the rigid endoscope 2 is made to make a tilting motion toward the side opposite to the surgeon 101, and FIGS. 7C and 7D illustrate a behavior of the distal arm (the distal arm 202 including the two arm portions 203 and 204) described in the Description of the Related Art section above resulting a behavior similar to that of the rigid endoscope 2, as a comparative example for the example. As is clear from the comparison, the first and fourth distal arm portions 55 and 58 of the distal arm 32 and the first and second arm portions 203 and 204 of the distal arm 202 move exhibiting behaviors substantially similar to each other.

According to such embodiment, the distal arm 32 that holds the rigid endoscope 2 includes a multi-joint articulated arm including the first to fourth distal arm portions 55 to 58 sequentially connected from the base portion 50 side, and the respective first to fourth distal arm portions 55 to 58 are configured so as to move on a vertical plane with the horizontal rotational shafts 60 to 63 as supports, enabling sufficient reduction in length of each of the distal arm portions 55 to 58 compared to, e.g., a case where a distal arm includes two arm portions, and thus, enabling a sufficient range of movement of the rigid endoscope 2 to be secured while the surgeon 101's view of, e.g., the monitor 7 is unobstructed (see FIGS. 3 to 6). In addition, the respective arm portions 55 to 58 move on a vertical plane with the respective horizontal rotational shafts 60 to 63 as supports, and thus, the area occupied by the distal arm 32 in the vicinity of the patient 100 is so small that operations in a surgery are not interrupted. In addition, behaviors of the respective distal arm portions 55 to 58 are linked by means of the linking mechanism so that the first distal arm portion 55 and the third distal arm portion 57 behave in parallel to each other, and the second distal arm portion 56 and the fourth distal arm portion 58 behave in parallel to each other, whereby the distal arm 32 can substantially make a motion exhibiting a behavior substantially equal to a motion resulting from combination of the rotary (swing) motion of the first distal arm portion 55 with the horizontal rotational shaft 60 as a support and the rotary (swing) motion of the fourth distal arm portion 58 with the virtual rotational shaft 79 as a support.

Here, the linking mechanism included in the distal arm 32 is not limited to that included in the above-described configuration, and arbitrary modifications are possible.

For example, in the configuration illustrated in FIG. 9, a first auxiliary arm portion 90 is arranged in parallel to a second distal arm portion 56, and one end portion of the first auxiliary arm portion 90 is rotatably and pivotally supported by a distal end portion of a first distal arm portion 55 via a horizontal rotational shaft 92, and the other end side of the first auxiliary arm portion 90 is rotatably and pivotally supported at a position part way through the third distal arm portion 57 via a horizontal rotational shaft 93. Consequently, the first auxiliary arm portion 90 provides a first parallelogram link 96 jointly with the first to third distal arm portions 55 to 57.

Also, a second auxiliary arm portion 91 is arranged in parallel to the third distal arm portion 57, and one end portion of the second auxiliary arm portion 91 is rotatably and pivotally supported at a position part way through the first auxiliary arm portion 90 via a horizontal rotational shaft 94, and the other end side of the second auxiliary arm portion 91 is pivotally supported by a proximal end portion of the fourth distal arm portion 58 via a horizontal rotational shaft 95. Consequently, the second auxiliary arm portion 91 provides a second parallelogram link 97 jointly with the third and fourth distal arm portions 57 and 58 and the first auxiliary arm portion 90.

Then, the first and second parallelogram links 96 and 97 provide a linking mechanism as interlocking means. Such configuration also enables provision of operations and effects similar to those of the above-described configuration using the first and second auxiliary arm portions 71 and 72.

Here, switches for cancelling a locked state provided by the respective locking mechanisms 80 to 82 are not limited to switches separately provided for the respective locking mechanisms 80 to 82, and for example, as illustrated in FIG. 9, a single switch 83 can be provided to cancel locked states of the respective locking mechanisms 80 to 82, and furthermore, the switches can be substituted with, e.g., non-illustrated foot switches.

Furthermore, the balancing means for cancelling out a moment around the horizontal rotational shaft 60, which is generated by the weight of the distal arm 32, is not limited to the above-described gas spring, and for example, as illustrated in FIG. 9, a weight 99 provided at the proximal end portion of the first arm portion 55 (more specifically, on the proximal end side relative to the horizontal rotational shaft 60) can be employed for the balancing means.

Figure 10:
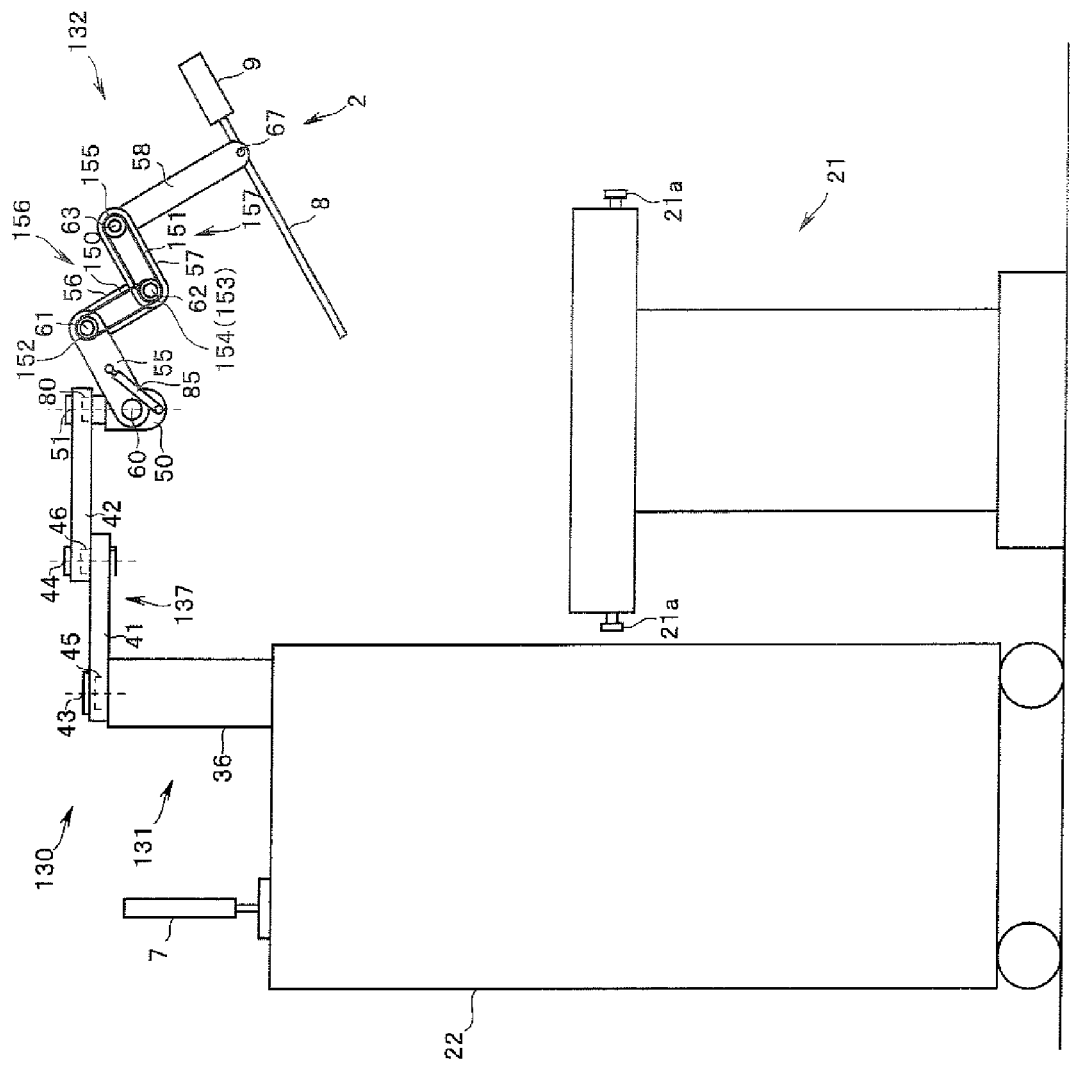
FIG. 10 relates to a second embodiment of the present invention and is a diagram of a schematic configuration of an endoscope holding apparatus.
Figure 12A:
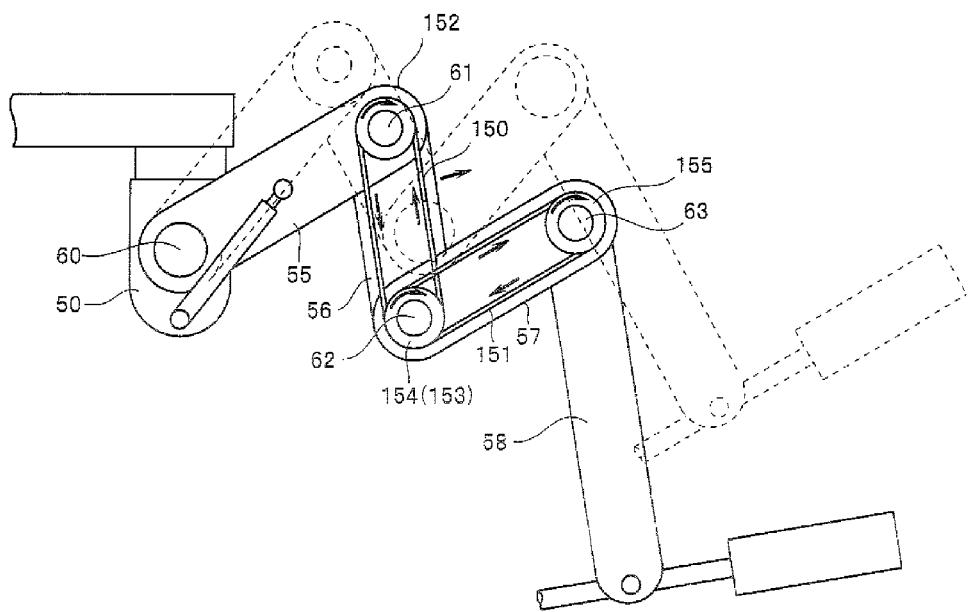
FIG. 12A relates to a second embodiment of the present invention and is an illustrative diagram of motion of an articulated arm.
Figure 12B:
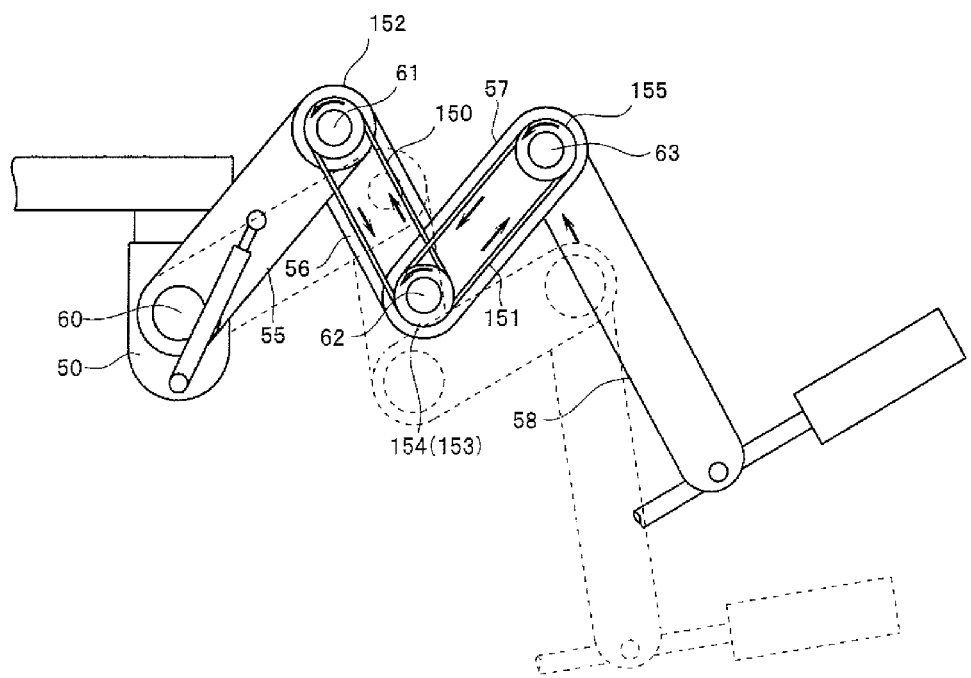
FIG. 12B relates to a second embodiment of the present invention and is an illustrative diagram of motion of an articulated arm.
Figure 13:
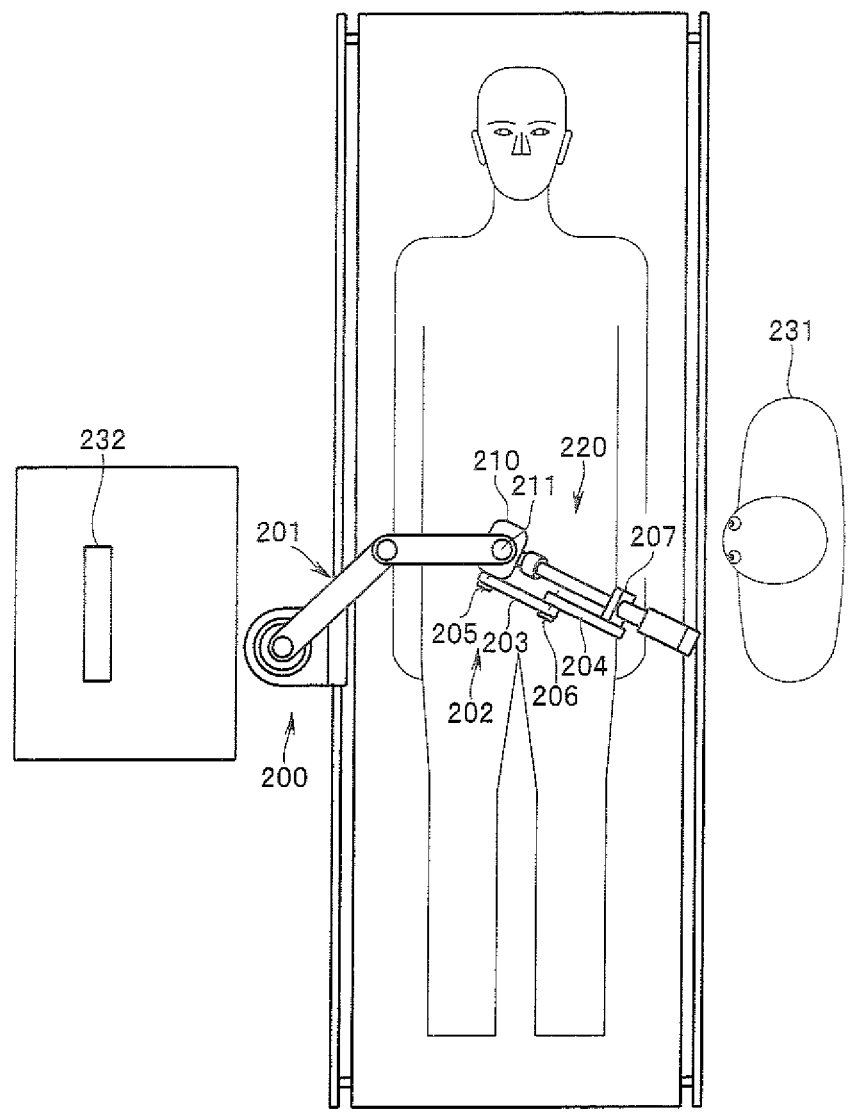
FIG. 13 is a plan view showing a relationship between a conventional endoscope holding apparatus and a surgeon.
Figure 14:
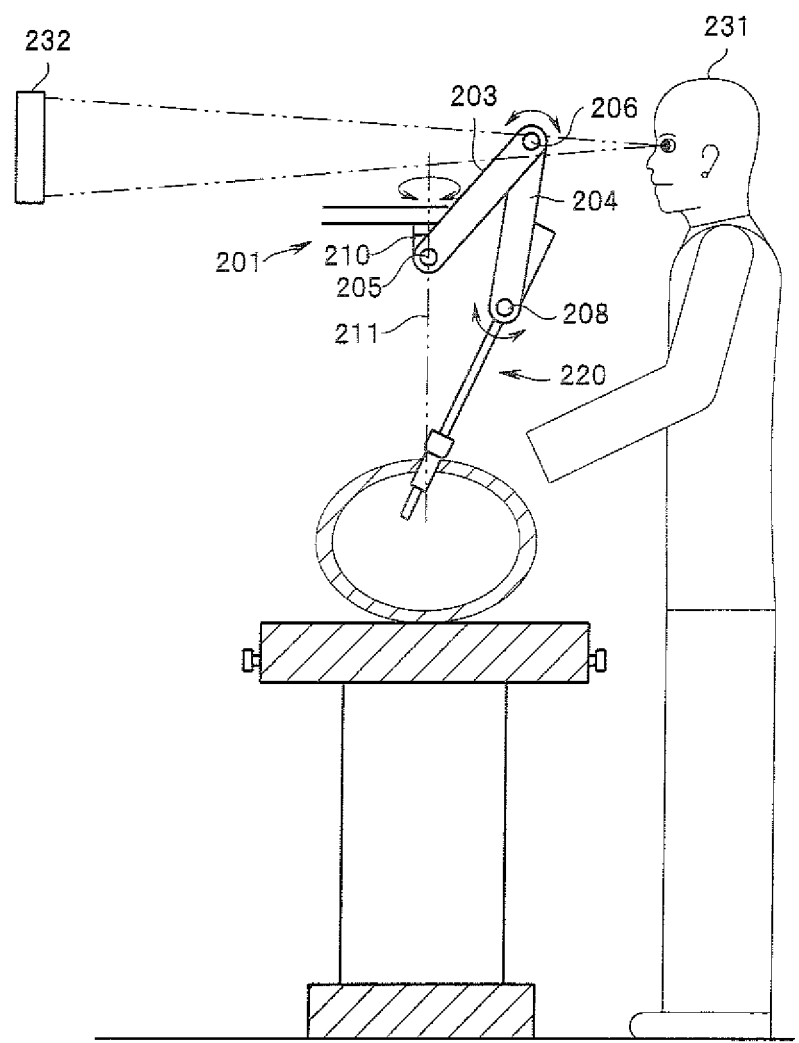
FIG. 14 is s a plan view showing a relationship between a conventional endoscope holding apparatus and a surgeon and is also an illustrative diagram of motion of an articulated arm.

Next, FIGS. 10 to 12B relate to a second embodiment of the present invention: FIG. 10 is a diagram of a schematic configuration of an endoscope holding apparatus; FIG. 11A is a side view showing a schematic configuration of an articulated arm; FIG. 11B is a cross-sectional diagram of a main part taken along line I-I in FIG. 11A; FIGS. 12A and 12B are illustrative diagrams of a motion of an articulated arm. In the present embodiment, components that are similar to those in the above-described first embodiment are provided with reference numerals that are the same as those of the first embodiment, and a description thereof will be omitted.

As illustrated in FIG. 10, an endoscope holding apparatus 130 according to the present embodiment employs a configuration in which the endoscope holding apparatus 130 is secured to a trolley 22 instead of the configuration in which an endoscope holding apparatus is detachably attached to a bed rail 21a via a bed attachment portion 35. More specifically, in the endoscope holding apparatus 130 according to the present embodiment, a strut 36 included in a stand 131 is provided so as to stand from a top surface of the trolley 22.

Furthermore, as illustrated in FIGS. 11A and 11B, pulley mechanisms 156 and 157 including first and second endless belts 150 and 151 as flexible power transmission means are provided on the distal arm 132 in the present embodiment, and the pulley mechanisms 156 and 157 provides a flexible transmission mechanism as interlocking means. Then, behaviors of the respective distal arm portions 55 to 58 are linked by means of the flexible transmission mechanism so that the first distal arm portion 55 and the third distal arm portion 57 behave in parallel to each other and the second distal arm portion 56 and the fourth distal arm portion 58 behave in parallel to each other.

For more specific description, on a side of the distal arm 132, a horizontal rotational shaft 61 that connects the first distal arm portion 55 and the second distal arm portion 56 is provided with a first pulley 152. As illustrated in FIG. 11B, the first pulley 152 is fastened to the first distal arm portion 55 via a screw 152a. Consequently, when the second distal arm portion 56 makes a rotary motion with the horizontal rotational shaft 61 as a support, the first pulley 152 is held integrally with the first distal arm portion 55 (in other words, the first pulley 152 rotates relative to the second distal arm portion 56).

Also, at a side of the distal arm 132, the horizontal rotational shaft 62 that connects the second distal arm portion 56 to the third distal arm portion 57 is provided with a second pulley 153 and a third pulley 154 in such a manner that the second pulley 153 and the third pulley 154 are overlapped with each other.

The second pulley 153 includes a pulley having a diameter equal to that of the first pulley 152. As illustrated in FIG. 11B, the second pulley 153 is fastened to the third distal arm portion 57 via a screw 153a. Consequently, when the third distal arm portion 57 makes a rotary motion with the horizontal rotational shaft 62 as a support, the second pulley 153 makes a rotary motion integrally with the third distal arm portion 57 (in other words, the second pulley 153 rotates relative to the second distal arm portion 56).

As illustrated in FIG. 11B, the third pulley 154 is fastened to the horizontal rotational shaft 62 via a screw 154a. Furthermore, the horizontal rotational shaft 62 is non-rotatably fastened to the second distal arm portion 56 via a screw 62a.

Consequently, when the third distal arm portion 57 makes a rotary motion with the horizontal rotational shaft 62 as a support, the third pulley 154 makes a rotary motion integrally with the second distal arm portion 56 (in other words, the third pulley 154 rotates relative to the third distal arm portion 57).

Furthermore, the horizontal rotational shaft 63 that connects the third distal arm portion 57 and the fourth distal arm portion 58 is provided with a fourth pulley 155. As illustrated in FIG. 11B, the fourth pulley 155 includes a pulley having a diameter equal to that of the third pulley 154. The fourth pulley is fastened to the horizontal rotational shaft 63 via a screw 155a. Also, the horizontal rotational shaft 63 is non-rotatably fastened to the fourth distal arm portion 58 via a screw 63a. Consequently, when the fourth distal arm portion 58 makes a rotary motion with the horizontal rotational shaft 63 as a support, the fourth pulley 155 makes a rotary motion integrally with the fourth distal arm portion 58 (in other words, the fourth pulley 155 rotates relative to the third distal arm portion 57).

Furthermore, a first endless belt 150 is looped around the first pulley 152 and the second pulley 153, and a second endless belt 151 is looped around the third pulley 154 and the fourth pulley 155.

Next, an operation of the endoscope holding apparatus 130 configured as described above will be described.

When a surgeon or the like operates switches 83a to 83c for respective locking mechanisms 80 to 82 to unlock the respective portions, and, for example, grasps the rigid endoscope 2 and moves the rigid endoscope 2 downward, as illustrated in FIG. 12A, the fourth distal arm portion 58 makes a rotary (swing) motion clockwise in the figure (in a direction of movement away from the surgeon 101) with the horizontal rotational shaft 63 as a support. When the fourth pulley 155 rotates clockwise integrally with the fourth distal arm portion 58 in association with the rotation, a force of the rotation is transmitted to the third pulley 154 via the second endless belt 151. Consequently, the second distal arm portion 56 makes a rotary (swing) motion with the horizontal rotational shaft 61 as a support, maintaining a state in parallel to the fourth distal arm portion 58.

Furthermore, in association with the motion of the fourth distal arm portion 58, the third distal arm portion 57 makes a rotary (swing) motion clockwise in the figure with the horizontal rotational shaft 62 as a support. When the second pulley 153 rotates clockwise integrally with the third distal arm portion 57 in association with the rotation, a force of the rotation is transmitted to the first pulley 152 via the first endless belt 150. Consequently, the first distal arm portion 55 makes a rotary (swing) motion with a horizontal rotational shaft 60 as a support, maintaining a state in parallel to the third distal arm portion 57.

Meanwhile, when the surgeon or the like, e.g., grasps the rigid endoscope 2 and moves the rigid endoscope 2 upward, as illustrated in FIG. 12B, the fourth distal arm portion 58 makes a rotary (swing) motion counterclockwise in the figure (in a direction of movement toward the surgeon 101) with the horizontal rotational shaft 63 as a support. When the fourth pulley 155 rotates counterclockwise integrally with the fourth distal arm portion 58 in association with the rotation, a force of such rotation is transmitted to the third pulley 154 via the second endless belt 151. Consequently, the second distal arm portion 56 makes a rotary (swing) motion with the horizontal rotational shaft 61 as a support, maintaining a state in parallel to the fourth distal arm portion 58.

Furthermore, in conjunction with the motion of the fourth distal arm portion 58, the third distal arm portion 57 makes a rotary (swing) motion counterclockwise in the figure with the horizontal rotational shaft 62 as a support. When the second pulley 153 rotates counterclockwise integrally with the third distal arm portion 57, a force of such rotation is transmitted to the first pulley 152 via the first endless belt 150. Consequently, the first distal arm portion 55 makes a rotary (swing) motion with the horizontal rotational shaft 60 as a support, maintaining a state in parallel to the third distal arm portion 57.

The present embodiment eliminates the need to secure, e.g., spaces for connection of auxiliary arm portions in the respective distal arm portions, and thus, enables a compact configuration of the respective distal arm portions 55 to 58 compared to a case where a linking mechanism is used. Accordingly, the present embodiment provides the effect of, e.g., more preferably making the surgeon 101's view unobstructed in addition to the effects provided by the above-described first embodiment. In addition, the weight of the entire distal arm 132 can be reduced compared to the case where the linking mechanism is employed.

Furthermore, the integration of the endoscope holding apparatus 130 with the trolley 22 enables, e.g., easy installation in an operating room.

It should be understood that the present invention is not limited to the above-described embodiment, and various modifications and applications are possible without departing from the spirit of the invention. Also, it should be understood that an endoscope holding apparatus may be provided by arbitrarily combining the respective configurations of the embodiments described above.

What is claimed is:

1. An endoscope holding apparatus adapted to hold an endoscope in which an insertion portion is inserted into an abdominal cavity via a trocar pierced through an abdominal wall, the apparatus comprising:
 a stand that allows a base portion to be supported immediately above the trocar pierced through the abdominal wall;
 a distal arm with a proximal end side thereof rotatably and pivotally supported by the base portion via only a vertical rotational shaft, the distal arm including a multi-joint arm including first, second, third and fourth distal arm portions sequentially connected from the base portion side, the first, second, third and fourth distal arm portions being sequentially connected in an M letter shape such that a horizontal rotational shaft that rotatably and pivotally supports the second distal arm portion and the third distal arm portion is positioned below a virtual intersection between the first distal arm portion and the fourth distal arm portion, the distal arm moving, the a vertical plane, an endoscope that is supported by an endoscope holding portion which is rotatably and pivotally supported only by the fourth distal arm portion, with the trocar serving as a support, via only a rotational shaft parallel to the horizontal shaft; and
 an interlocking section that links behaviors of the respective distal arm portions so that the first distal arm portion and the third distal arm portion behave in parallel to each other, and the second distal arm portion and the fourth distal arm portion behave in parallel to each other, thereby moving the distal arm with an angle formed by the first and fourth distal arm portions and an angle formed by the second and third distal arm portions consistently maintained to be equal to each other.

2. The endoscope holding apparatus according to claim 1, wherein the interlocking section includes a linking mechanism.

3. The endoscope holding apparatus according to claim 1, wherein the interlocking section includes a flexible transmission mechanism using a flexible power transmission section as a medium.

4. The endoscope holding apparatus according to claim 1, wherein the base portion is rotatably and pivotally supported by the stand via a vertical rotational shaft.

5. The endoscope holding apparatus according to claim 4, further comprising:
- a first locking mechanism capable of locking a motion between the stand and the base portion;
- a second locking mechanism capable of locking a motion between the base portion and the first distal arm portion; and
- a third locking mechanism capable of any one of a motion between the first distal arm portion and the second distal arm portion, a motion between the second distal arm portion and the third distal arm portion and a motion between the third distal arm portion and the fourth distal arm portion.

6. The endoscope holding apparatus according to claim 1, further comprising a balancing section that balances out a moment generated by a weight of the distal arm.

7. The endoscope holding apparatus according to claim 6, wherein the balancing section includes a gas spring.

8. The endoscope holding apparatus according to claim 6, wherein the balancing section includes a weight.

9. An endoscope holding apparatus adapted to hold an endoscope in which an insertion portion is inserted into an abdominal cavity via a trocar pierced through an abdominal wall, the apparatus comprising:
- a stand that allows a base portion to be supported immediately above the trocar pierced through the abdominal wall;
- a distal arm with a proximal end side thereof rotatably and pivotally supported by the base portion via only a vertical rotational shaft, the distal arm including a multi-joint arm including first, second, third and fourth distal arm portions sequentially connected from the base portion side, the distal arm including a holding portion for holding an endoscope on a distal end side of the fourth distal arm portion, a virtual intersection between the first distal arm portion and the fourth distal arm portion being on a proximal end side of the fourth distal arm portion, the distal arm moving the endoscope on a vertical plane with the trocar serving as a support, the holding portion being rotatably and pivotally supported only by the fourth distal arm portion via only a rotational shaft parallel to the horizontal rotational shaft; and
- an interlocking section that links behaviors of the respective distal arm portions so that the first distal arm portion and the third distal arm portion behave in parallel to each other, and the second distal arm portion and the fourth distal arm portion behave in parallel to each other, thereby moving the distal arm with an angle formed by the first and fourth distal arm portions and an angle formed by the second and third distal arm portions consistently maintained to be equal to each other.

* * * * *